United States Patent [19]

Rinehold

[11] Patent Number: 4,930,535
[45] Date of Patent: Jun. 5, 1990

[54] FOLDING LEAF VALVE AND METHOD OF MAKING

[75] Inventor: Elizabeth A. Rinehold, Santa Barbara, Calif.

[73] Assignee: McGhan Medical Corporation, Santa Barbara, Calif.

[21] Appl. No.: 372,222

[22] Filed: Jun. 23, 1989

Related U.S. Application Data

[63] Continuation-in-part of Ser. No. 51,508, May 14, 1987, abandoned.

[51] Int. Cl.⁵ ............................................. F16K 15/00
[52] U.S. Cl. ..................................... 137/15; 137/315; 137/855; 604/256; 251/149.1; 623/8
[58] Field of Search ............................... 604/247, 256; 251/149.1; 137/855, 223, 15, 315; 623/8

[56] References Cited

U.S. PATENT DOCUMENTS

| | | | |
|---|---|---|---|
| 1,702,974 | 2/1929 | MacDonald | 137/846 |
| 2,516,578 | 7/1950 | Kreiner | 137/855 |
| 2,700,980 | 2/1955 | Andrews | 137/223 |
| 3,410,300 | 11/1968 | Mondano | 137/223 |
| 4,143,853 | 3/1979 | Abramson | 251/149.1 |
| 4,387,879 | 6/1983 | Tauschinski | 604/247 |
| 4,416,267 | 11/1983 | Garren et al. | 128/1 R |
| 4,589,869 | 5/1986 | Wernborg | 604/247 |
| 4,626,245 | 12/1986 | Weinstein | 251/149.1 |
| 4,662,883 | 5/1987 | Bell et al. | 623/8 |
| 4,694,827 | 9/1987 | Weiner et al. | 128/303 R |
| 4,775,379 | 10/1988 | Fogarty et al. | 138/118 |

FOREIGN PATENT DOCUMENTS

| | | | |
|---|---|---|---|
| 391222 | 1/1902 | France | 137/223 |
| 9698 | of 1902 | United Kingdom | 137/223 |

Primary Examiner—A. Michael Chambers
Attorney, Agent, or Firm—Michael G. Petit

[57] ABSTRACT

A leaf valve folds upon itself to provide positive sealing of a pressurized chamber under a variety of pressure conditions. In particular, the valve stem folds to effectively close the lumen and provide a positive seal even at low differential pressure. A method of making the valve is descirbed.

4 Claims, 1 Drawing Sheet

FOLDING LEAF VALVE AND METHOD OF MAKING

This is a continuation-in-part Ser. No. 07/051,508, filed May 14, 1987 now abandoned.

SUMMARY

This application is a C-I-P of application Ser. No. 07/051,508 filed 05/14/87, now abandoned.

A self-kinking leaf valve suitable for applications requiring periodic passage of an intubation catheter is described. The valve retracts upon itself by discrete folding when a catheter into the interior chamber of an inflatable envelope such as an intragastric balloon is withdrawn thus providing a positive seal. A method of making the valve is described.

BACKGROUND OF THE INVENTION

1. Field of the Invention

The present invention is an improved leaf valve containing a normally closed lumen which, when affixed to the interior surface of a chamber defined by a surrounding envelope such as an intragastric balloon and fully extended, as for example, by the passage of a tube or catheter through the lumen, provides a direct path to the interior of the chamber. When the tube or catheter is withdrawn from the valve, the lumen of the valve stem folds on itself, accordion style, to positively close the lumen and prevent leakage from the chamber.

2. Background of the Invention

Implantable devices requiring external access to an interior chamber are well known in medicine. Tissue expander devices, for example, comprise an inflatable envelope of a biocompatible elastomer. Following surgical implantation beneath the skin, the device is gradually inflated by injection of a fluid into the chamber of the device through a self-sealing septum. As the implanted device gradually expands, it causes the overlying skin to stretch thus generating a flap of skin which may be used for reconstructive surgery.

A similar device is the intragastric balloon used to treat patients suffering from morbid obesity such as described by Garren et al in U.S. Pat. No. 4,416,267 and by Weiner et al in U.S. Pat. No. 4,694,827. Such devices are inserted empty, usually by means of an endoscope, into the stomach. Following deployment of the device within the stomach, the balloon is usually inflated by injecting a fluid into the interior chamber of the balloon through a catheter. When the balloon is fully inflated, the intubation catheter is removed by pulling it free of the balloon and out through the mouth. When the tube is pulled out of the balloon through a leak-proof valve, the balloon must remain fully inflated in the stomach for months. If the valve leaks, the balloon may pass through the stomach into the intestine where serious bowel obstruction may occur. The design of the valve that seals the envelope of such a balloon upon withdrawal of the inflation tube must provide a positive seal under a variety of pressure differentials.

Leaf valves are well known in the art (Andrews, MM, U.S. Pat. No. 2,700,980; MacDonald, W.W., U.S. Pat. No. 1,702,974). Their principle of operation and use is similar to flap valves. In general, they are used to seal a conduit through a surface across which a differential pressure exists thus preventing transport of fluid from the high pressure side to the low pressure side.

While flap valves are molded from an elastomer to fit snugly against the surface to be sealed, leaf valves are affixed to the surface so that the conduit passing therethrough the lumen is substantially parallel to the direction of travel of a catheter passed through the leaf valve.

Leaf valves, unlike flap valves, possess a conduit or lumen passing throught the stem, the walls of which are comprised, at least in part, of an elastomeric material. External pressure on the stem walls forces the elastomeric material to close upon itself thus effectively sealing the conduit. In other words, a positive seal is only possible when the pressure outside the stem wall is sufficient to deform the walls inward to close the conduit.

An improved curling or pig-tail leaf valve has been described (U.S. Pat. No. 4,775.379) by Terence M. Fogarty, in which two strips of elastomer, one of which is initially stretched, are molded together to form a stem leaving a conduit down the length of the valve stem. When the stem is removed from the mold, it curls up due to the difference in tension of the forming parts. When the stem curls up, it closes the conduit by pressing the walls together continuously along the length of the valve stem. The curling leaf valve has the advantage that it is more resistant to leakage in the absence of a pressure differential but it still requires a pressure differential for positive sealing. Thus, a valve is needed which will positively seal without the absence of a pressure differential. The difference between the self-kinking valve of the current invention and prior art valves can be viewed instructively by drawing an analogy to stopping the flow of water through a garden hose: prior art valves are analogous to stepping on the hose to stop the flow of water therethrough while the valve of the current invention stops the flow by kinking the hose.

SUMMARY OF THE PRESENT INVENTION

To immunize the leaf valve from leakage in the absence of a pressure differential, kinking of the stem and resulting positive closure of the conduit is desirable. The kink can be realized by discrete folding of the valve stem upon itself through an angle greater than 90 degrees. The preferred embodiment of the valve of the present invention resembles a silicone straw that has been flattened and folded upon itself end to end, accordion fashion. A flange at one end of the "folded straw" provides (a) an opening to the lumen of the valve stem and (b) means for attaching the valve to an envelope containing an interior chamber such as an intragastric balloon. Since the valve is made of silicone (vulcanized in the folded configuration) the valve stem is normally kinked thus closing the lumen passing therethrough. During use, the (normally folded) valve stem extends into the interior of a chamber. The opposing end of the valve stem to which the flange is vulcanized is attached to the surface of the envelope housing the chamber. The valve may be opened by passage of a catheter through the conduit defined by the lumen of the valve stem. When the cathether is subsequently withdrawn, the valve stem closes discretely upon itself, accordion fashion, thereby kinking the conduit and preventing leakage even in the absence of a pressure differential. The present invention can be best described by reference to the drawings.

DESCRIPTION OF THE PREFERRED EMBODIMENT

Figure 1:
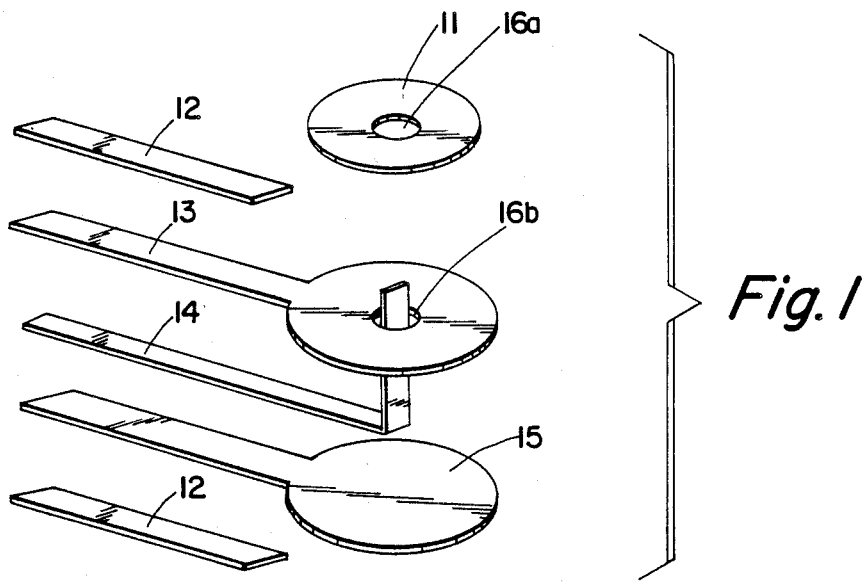
FIG. 1. Scheme of organization of the folding leaf valve elements prior to forming and vulcanization.
Figure 2:
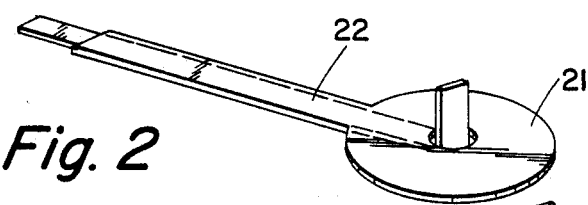
FIG. 2. Perspective view of assembled folding leaf valve prior to vulcanization.

Referring now to FIG. 1, lumen forming releasing material A (14) is interposed between two raw unvulcanized silicone strips (13 and 15) which have been reinforced at the exterior lumen orifice (15 and 16) by the addition of a raw patch of silicon rubber (11) which has a hole (16a) which will form the exterior lumen orifice. The two strips of raw unvulcanized silicone rubber (13 and 15) are identical except that one strip (13) has a hole cut out of it (16b) which will become the inner exterior lumen orifice. The aforesaid subassembly is further interposed between two additional layers of releasing material B (12) to complete the pre-vulcanized assembly (FIG. 2).

Figure 3:
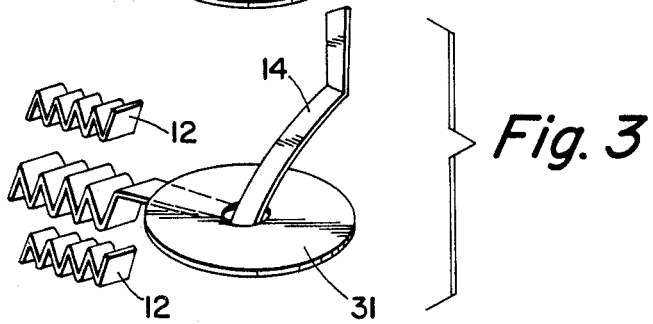
FIG. 3. Perspective view of folding leaf valve following vulcanization with attaching insert in place and releasing material removed.
Figure 4:
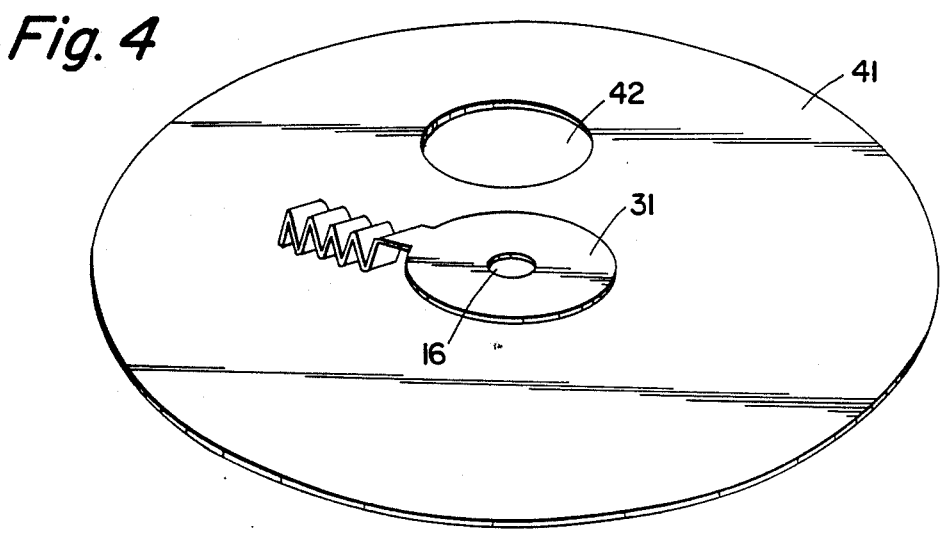
FIG. 4. Perspective view of attachment of folding leaf valve to the interior surface of a chamber.

The assembly (FIG. 2) has two distinct parts: a reinforced head or flange (21) and a stem (22). Stem (22) is folded back and forth upon itself and the folded assembly (not shown) is placed in a vulcanizing press (not shown). After remaining in the press for a time sufficient to effect vulcanization of all contacting elastomer surfaces, the vulcanized assembly (FIG. 3) is removed and release material B (FIG. 3, 12) is peeled off and lumen forming release material A (FIG. 3, 14) is pulled out. The raw patch (11) is then placed (not shown) over reinforced head (21) so that its exterior lumen orifice (16a) coincides with the exterior lumen orifice of the reinforcing head (16b) and the resulting folding leaf valve ((31) FIG. 4) is then affixed to the interior surface of the chamber (41) by vulcanization to cover opening (42). The raw patch (11) effects a strong permanent seal between the valve's reinforced head (21) and the interior surface of the chamber receiving the valve (41). A catheter (not shown) may then be passed through exterior lumen orifice (16) through the lumen (23) of the valve stem into the interior of the chamber.

When a catheter is passed through the valve, the stem unfolds to accommodate its passage. When the catheter is subsequently withdrawn, even months later, the stem discretely folds upon itself to effectively seal the lumen (23) passing therethrough.

What we claim is:

1. A method of making a folding leaf valve comprising the steps of:
   (a) placing a strip of lumen-forming releasing material A between two wider strips of raw elastomer to form a first laminate.
   (b) layering onto both outer surfaces of said first laminate a releasing material B to form a second laminate,
   (c) folding said second laminate over itself at least once; and
   (d) heating said folded second laminate for a period of time sufficient to vulcanize all elastomer surfaces in contact with each other.

2. The method of claim 1 wherein the dimensions of said lumen-forming releasing material are chosen to accommodate the passage of a catheter through the lumen formed thereby.

3. The method of claim 1 wherein the thickness of said first releasing material and said second releasing material is the same.

4. A valve which is self-sealing to the track of a fill-tube removed therefrom, said valve thereafter providing positive closure of a conduit passing therethrough by folding discretely upon itself through an angle greater than 90 degrees comprising:
   (a) a discretely folded elastic valve stem made from an elastomeric polymer; and
   (b) a conduit passing through said elastic valve stem; wherein the valve stem contains a plurality of folds, said folds being sequentially reversed 180 degrees to form a zigzag valve stem and wherein the axis of folding of the valve stem is perpendicular to the direction of the conduit.

* * * * *